United States Patent [19]
Kaplan et al.

[11] Patent Number: 6,100,086
[45] Date of Patent: Aug. 8, 2000

[54] TRANSGENE EXPRESSION SYSTEMS

[75] Inventors: Johanne Kaplan, Sherborn; Donna Armentano, Belmont; Richard J. Gregory, Westford, all of Mass.

[73] Assignee: Genzyme Corporation, Cambridge, Mass.

[21] Appl. No.: 08/839,679

[22] Filed: Apr. 14, 1997

[51] Int. Cl.$^7$ .............................. C12N 15/86; C07J 9/00
[52] U.S. Cl. ................ 435/320.1; 435/457; 435/458; 536/23.72; 552/544
[58] Field of Search ................ 435/320.1, 69.1, 435/455, 456, 457, 458; 424/450, 93.2, 93.6; 536/23.72, 23.1, 24.1; 552/544; 514/44

[56] References Cited

FOREIGN PATENT DOCUMENTS

| | | |
|---|---|---|
| WO9412649 | 6/1994 | WIPO . |
| WO 96/14061 | 5/1996 | WIPO . |
| WO 96/30534 | 10/1996 | WIPO . |

OTHER PUBLICATIONS

W. French Anderson, Nature, vol. 392, pp. 25–30, Apr. 30, 1998.
Kaplan et al., Human Gene Therapy, vol. 8, pp. 45–56, Jan. 1, 1997.
Zabner et al., J. Clin. Invest., vol. 97, pp. 1504–1511, Mar. 1996.
Ronald G. Crystal, Science, vol. 270, pp. 404–410, Oct. 20, 1995.
Verma et al., Nature, vol. 389, pp. 239–242, Sep. 18, 1997.
Orken et al., "Report and Recommendations of the Panel to Assess the NIH Investment in Research on Gene Therapy", Dec. 7, 1995.
Armentano, D., et al. Effect of the E4 Region on the Persistence of Transgene Expression from Adenovirus Vectors. Journal of Virology, vol. 71, 1997, 2408–2416.
Horwitz, M.S. Adenoviridae and Their Replication. Virology, Second Edition, 1990, 1679–1721.
Huang, M–M., et al. Adenovirus Early Region 4 Encodes Two Gene Products with Redundant Effects in Lytic Infection. Journal of Virology, vol. 63, 1989, 2605–1615.
Kaplan, J.M., et al. Characterization of Factors Involved in Modulating Persistence of Transgene Expression from Recombinant Adenovirus in the Mouse Lung. Human Gene Therapy, vol. 8, 1997, 45–56.
Kaplan, J.M., et al. Humoral and cellular immune responses of nonhuman primates to long–term repeated lung exposure to Ad2/CFTR–2. Gene Therapy, vol. 3, 1996, 117–127.
Kleinberger, T., et al. Adenovirus E4orf4 Protein Binds To Protein Phosphatase 2A, And The Complex Down Regulates E1A–Enhanced junB Transcription. Journal of Virology, vol. 67, 1993, 7556–7560.
Wang, Q., et al. A packaging cell line for propagation of recombinant adenovirus vectors containing two lethal gene–region deletions. Gene Therapy, vol. 2, 1995, 775–783.
Armentano, D., et al. Characterization of an Adenovirus Gene Transfer Vector Containing an E4 Deletion. Human Gene Therapy, vol. 6, 1995, 1343–1353.
Scaria, A., etal., Antibody to CD40 ligands inhibits both humoral and cellular immune responses to adenoviral vectors and facilitates repeated administration to mouse airway. Gene Therapy, vol. 4, 1997, 611–617.
Kaplan, J. et al. Transient Immunosuppression with Deoxyspergualin Improves Longevity of Transgene Expression and Ability to Readminister Adenoviral Vector to the Mouse Lung, Human Gene Therapy, vol. 8, 1997, 1095–1104.
Lui, Ru, et al. The Transcription Factor YY1 Binds to Negative Regulatory Elements In The Human Cytomegalovirus Major Immediate Early Enhancer/Promoter and Mediates Repression In Nonpermissive Cells, Nucleic Acids Research, 1994, vol. 22, No. 13, 2453–2459.
Liu, Bo, et al. A cis–Acting Element In The Major Immediate–Early (IE) Promoter Of Human Cytomegalovirus Is Required For Negative Regulations By IE2, Journal of Virology, Feb. 1991, vol. 65, No. 2, 897–903.
Lang, A. etal., Factors Influencing Physiological Variations In The Activity Of The Rous Sarcoma Virus Long Terminal Repeat, Virology 196, 1993, 564–575.
Wilkinson, G.W.G., et al., Constitutive And Enhanced Expression From The CMV Major IE Promoter In A Defective Adenovirus Vector, Nucleic Acids Research, vol. 20, No. 9, 2233–2239.
Gualberto, A., et al., Functional Antagonism Between YY1 And The Serum Respone Factor, Molecular And Cellular Biology, Sep. 1992, vol. 12, No. 9, 4209–4214.

*Primary Examiner*—David Guzo
*Attorney, Agent, or Firm*—Baker and Botts, L.L.P.

[57] ABSTRACT

The present invention relates to transgene expression systems, related pharmaceutical compositions, and methods of making and using them. Preferred systems employ an adenovirus transgene expression vector comprising DNA sequence encoding a transgene which codes for a desired product, expressibly contained within an adenovirus vector containing at least a portion of the E3 region and certain portions of the E4 region. The E4 portions comprise the open reading frame sequence known as E4ORF3 and at least one other portion of E4. Preferably the E4 portion of the vector (or "E4 cassette") includes E4ORF3 and at least one other portion selected from E4ORF4, E4ORF6/7 and E4ORF3/4. The invention has a number of important features including improving persistency of transgene expression in a desired host cell. The transgene expression systems of the present invention are useful for a variety of applications including providing persistent cellular expression of the transgene in vitro and in vivo.

15 Claims, 6 Drawing Sheets

TRANSGENE EXPRESSION SYSTEMS

FIELD OF THE INVENTION

The present invention relates to transgene expression systems, related pharmaceutical compositions, and methods of making and using them. Preferred systems employ an adenovirus transgene expression vector comprising DNA sequence encoding a transgene which codes for a desired product, expressibly contained within an adenovirus vector containing at least a portion of the E3 region and certain portions of the E4 region. The E4 portions comprise the open reading frame sequence known as E4ORF3 and at least one other portion of E4. Preferably the E4 portion of the vector (or "E4 cassette") includes E4ORF3 and at least one other portion selected from E4ORF4, E4ORF6/7 and E4ORF3/4. The invention has a number of important features including improving persistency of transgene expression in a desired host cell. The transgene expression systems of the present invention are useful for a variety of applications including providing persistent cellular expression of the transgene in vitro and in vivo.

BACKGROUND OF THE INVENTION

Adenovirus is a non-enveloped, nuclear DNA virus with a genome of about 36 kb. The viral genes are classified into early (known as E1–E4) and late (known as L1–L5) transcriptional units, referring to the generation of two temporal classes of viral proteins. See generally, Horwitz, M. S., "Adenoviridae and Their Replication," in *Virology*, 2nd edition, Fields et al., eds., Raven Press, New York, 1990.

Recombinant adenoviruses have advantages for use as transgene expression systems, including tropism for both dividing and non-dividing cells, minimal pathogenic potential, ability to replicate to high titer for preparation of vector stocks, and the potential to carry large inserts (see e.g., Berkner, K. L., *Curr. Top. Micro. Immunol.*, 158:39–66 (1992); Jolly D., *Cancer Gene Therapy*, 1:51–64 (1994)).

Adenovirus vectors can accommodate a variety of transgenes of different sizes. For example, about an eight (8) kb insert can be accommodated by deleting regions of the adenovirus genome dispensable for growth (e.g., E3). Development of cell lines that supply non-dispensable adenovirus gene products in trans (e.g., E1, E2a, E4) has allowed insertion of a variety of transgenes throughout the adenovirus genome (see e.g. Graham, F. L., *J. Gen. Virol.*, 36:59–72 (1977); Imler et al., *Gene Therapy*, 3:75–84 (1996)). For example, the p53, dystrophin, erythropoietin, ornithine transcarbamylase, adenosine deaminase, interleukin-2, α1antitrypsin, thrombopoietin, and cytosine deaminase genes have all been individually inserted into the adenovirus genome for making expression vectors.

The natural tropism of adenoviruses for respiratory tract cells has made them attractive gene therapy vectors for the treatment of cystic fibrosis (CF): the most common autosomal recessive disease in Caucasians. In CF, mutation of the cystic fibrosis transmembrane conductance regulator (CFTR) gene disturbs cAMP-regulated Cl⁻ channel function, resulting in pulmonary dysfunction. The CFTR gene has been introduced into adenovirus vectors to treat CF in several animal models and human patients. Particularly, studies have shown that adenovirus vectors are fully capable of delivering CFTR to nasal epithelia of CF patients, as well as the airway epithelia of cotton rats and primates. See e.g., Zabner et al., *Nature Genetics*, 6:75–83 (1994); Rich et al., *Human Gene Therapy*, 4:461–476 (1993); Zabner et al., *Cell*, 75:207–216 (1993); Zabner et al., *Nature Genetics*, 6:75–83 (1994); Crystal et al., *Nature Genetics*, 8:42–51 (1994); Rich et al., *Human Gene Therapy*, 4:461–476 (1993).

Importantly, recent studies have demonstrated that it is possible to restore a functioning chloride ion channel in CF patients by providing an adenoviral vector encoding CFTR to airway epithelia cells (Zabner et al., *J. Clin. Invest.*, 97:1504–1511 (1996)).

However, in vitro and in vivo studies have pointed to opportunities to further improve such vectors. For example, transgene expression from adenovirus vectors is often transient. Persistent transgene expression is highly desirable in gene therapy settings, especially those seeking to alleviate chronic or hereditary disease in mammals. At least some of the limitations are due to induction of a cell-mediated immune response against infected cells. In particular, cytotoxic T lymphocytes (CTLs) have been detected against antigenically expressed viral proteins encoded by adenovirus vectors, even though such vectors are replication defective. CTLs have also been detected against immunogenic transgene products. Cytotoxic T lymphocytes have the potential destroy or damage cells harboring the adenovirus vectors, thereby causing loss of transgene expression. Cell destruction can also cause inflamation which is also detrimental to the tissues involved. The cell-mediated immune response can pose a potentially serious obstacle to therapies requiring high dosages, which are likely to elicit more potent immune responses. See J. Kaplan et al., *Human Gene Therapy* 8:45–56 (1997); Y. Yang et al., *Proc. Nat. Acad. Sci.* 91:4405–11(1994); Y. Yang et al., *J. Virol.* 70:7202 (1996).

Various strategies have been used to minimize cell-mediated immune responses induced by adenovirus vectors. Generally, the strategies include modulation of the host immune response itself or engineering adenovirus vectors with a decreased capacity to induce immune responses.

For example, co-administration of immunosuppressive agents and adenovirus vectors have been reported to prolong persistence of transgene expression (Fang et al., *Hum. Gene Ther.*, 6:1039–1044 (1995); Kay et al., *Nature Genetics*, 11:191–197 (1995); Zsellenger et al., *Hum. Gene Ther.*, 6:457–467 (1995)).

In another approach, modification of adenovirus genome sequences in recombinant vectors has been used in attempts to decrease recognition of the vector by the immune system (see e.g., Yang et al., *Nature Genetics*, 7:362–369 (1994); Lieber et al., *J. Virol.*, 70:8944–8960 (1996); Gorziglia et al., *J. Virol.*, 70:4173–4178 (1996); Kochanek et al., *Proc. Natl. Acad. Sci. USA*, 93:5731–5736 (1996); Fisher et al., *Virology*, 217:11–22 (1996)).

The choice of promoter or transgene may also influence persistence of transgene expression from adenovirus vectors (see e.g., Guo et al., *Gene Therapy*, 3:801–802 (1996); Tripathy et al., *Nature Med.*, 2:545–550 (1996)).

Persistence of transgene expression from adenovirus vectors has been reported to be influenced by the adenovirus E3 gp19K protein. That protein can complex with MHC Class I molecules in the endoplasmic reticulum, thereby preventing both cell surface presentation of viral antigens and killing of transduced cells by cytotoxic T-lymphocytes (CTLs) (Wold et al., *Trends Microbiol.*, pp. 437–443, (1994)). However, approaches based on that knowledge have only achieved limited success.

Another problem which has faced researchers who are attempting to utilize viral vectors for gene therapy has been the size of the heterologous DNA which can be inserted into the modified viral genome. Early work involving insertion of heterologous genes in the area of E1 deletion resulted in vectors which were difficult to produce in sufficient quantities to permit continued clinical testing. See, e.g., D. Armentano et al., *Hum. Gene Ther.,* 6:1343 at 1344 (1995). While it is possible to possible to produce viral vectors which contain adenoviral DNA that is longer than the wild type genome length, the ability to replicate such vectors can decrease precipitously when the wild type genome length is substantially exceeded.

Accordingly, there is a need to develop and produce transgene expression vectors that have a genome whose size permits packaging that provides persistent transgene expression and minimizes cell-mediated immune reactions against cells containing the vectors. Such vectors would have a variety of uses, including use as gene transfer vectors in gene therapy.

SUMMARY OF THE INVENTION

The present invention relates to transgene expression systems and related pharmaceutical compositions and methods of making and using same. For example, in one aspect, the invention relates to an adenovirus transgene expression vector comprising DNA sequence encoding a transgene contained within an adenovirus vector in which the adenovirus vector contains at least a portion of the E3 region, and a modified E4 region. The modified E4 region may include only E4ORF4, or preferably, the modified E4 region contains at least E4ORF3 and at least one other portion of the E4 region. The term "modified E4" as used herein refers to an E4 region which has at least one deletion. Preferably, the size of the deletion(s) is (are) sufficient, taking into consideration any deletions elsewhere in the viral genome and also any added DNA, such that added heterologous DNA of the transgene(s) and associated promoters, enhancers and other transcriptional control elements, that the size of the resulting viral vector is typically less than about 110%, more preferably less than about 105%, most preferably less than about 101% of the size of the wild type virus genome. Preferably the deletion comprises at least one E4 open reading frame, although deletions in non-ORF portions of the E4 region can also be utilized. As indicated above, some modified E4 regions of the vectors of the present invention require expression from E4ORF3, and at least one additional portion of the E4 region. More preferably the E4 deletion comprises a plurality of open reading frames. Optionally, E4ORF6 may be deleted.

For example, a deletion includes removal of an ORF by frameshift mutation or knock-out which does not effect an open reading frame of another ORF.

In another aspect, the invention relates to an adenovirus transgene expression vector comprising DNA sequence encoding a transgene contained within an adenovirus vector in which the adenovirus vector contains at least a portion of the E3 region, and E4ORF4, or a modified E4 region which contains at least E4ORF4.

Preferably the modified E4 portion included in the vector of the present invention (or "E4 cassette") includes E4ORF3 and at least one other portion selected from E4ORF4, E4ORF6/7 and E4ORF3/4. Preferred parts of the E4 cassette are E4ORF3 and E4ORF4, E4ORF3 and E4ORF6/7, and E4ORF3 and E4ORF3/4. The modified E4 portion may also comprise E4ORF6. Thus far, the most preferred combination for persistent transgene expression from mammalian cells transformed with the vectors of the present invention is the combination of E3 with E4ORF3 and E4ORF4. The transgene expression system facilitates persistent expression of the transgene in cells and protects the cells from cell-mediated immune responses. The invention also features pharmaceutical compositions that comprise the transgene expression system and methods for using of such compositions to deliver therapeutic transgenes to desired cells. The invention further features methods for the production of the transgene expression system as well as methods for using the transgene expression system to express a transgene in a mammal, and methods of protecting cells expressing transgenes from cell-mediated immune responses.

We have developed a transgene expression system that facilitates persistent expression of transgenes in cells or groups of cells (e.g., tissue). In general, the transgene expression system persistently expresses a desired transgene in the presence of expression of at least a portion of the adenovirus E3 region ("E3 cassette") and a modified E4 region, preferably E4ORF3 and at least one other portion of E4. The transgene expression system achieves persistent transgene expression and protects cells expressing the transgene from cell-mediated immune responses, thereby providing more stable transgene expression in the cells. Accordingly, the present transgene expression system has a variety of uses, including use as a gene transfer system for providing desired transgenes to cells in vitro and in vivo.

Thus, in one aspect of the invention, transgene expression systems are provided individually comprising (a) DNA sequence encoding a transcription unit comprising a transgene operably linked to expression control sequences, (b) at least a portion of adenovirus E3 region, and (c) E4ORF3 and least one other portion of E4. In this aspect, the transgene expression system facilitates persistent expression of the transgene in cells and protects the cells expressing the transgene from cell-mediated immune responses that can potentially damage or destroy the cells harboring the transgene expression system (i.e., transduced cells). Accordingly, use of the transgene expression system improves transgene expression, e.g., by prolonging survival of cells expressing the transgene, and by reducing inflammation caused by the destruction of such cells.

In general, the transgene expression systems of the present invention provide significant advantages. For example, use of prior transgene expression systems typically stimulates host immune responses (e.g., CTLs, inflammation) that damage or destroy transduced cells expressing a desired transgene. In contrast, the present transgene expression systems provide persistent transgene expression while minimizing loss of expression caused by cell-mediated immune responses. Use of the prior transgene expression systems in high dosages typically induced pronounced cell-mediated immune responses against transduced cells. In contrast, the present transgene expression systems minimizes the susceptibility of transduced cells to cell-mediated immune responses, thereby making the present invention attractive, e.g., for use in gene therapy treatments requiring high or multiple dose protocols.

Additionally, prior transgene expression systems using recombinant adenovirus typically required high multiplicities of infection (MOIs) for efficient use. Often, high inputs of the virus killed transduced cells e.g., by introducing cytotoxic amounts of viral protein. In contrast, the present transgene expression system provides the opportunity to achieve persistent transgene expression without relying on undesirable amounts of input virus. Thus, use of the present transgene expression systems improve viability of cells expressing transgenes.

Generally, the transgene expression systems of the present invention provide persistent transgene expression in transduced mammalian cells, due at least in part to the presence of the adenovirus E3 region, at least (but not restricted to) the portion thereof coding for the gp19K gene product of adenovirus E3 region. Persistence can also be improved by inclusion in the vector of those portions of the E3 region which provide one or more of the following: the 14.7 k protein, the 10.4 k protein, and the 14.5 k protein.

Persistence can also be improved by including the E4ORF3 and E4ORF4 or other portion of the adenovirus E4 region. The presence of these DNA segments in the vector facilitates persistent expression of the transgene in cells while minimizing or eliminating destruction by the cell-mediated immune responses against cells expressing the transgene.

In preferred embodiments, transgene expression systems of the present invention are provided as replication-defective adenovirus vectors. That is, the replication-defective vectors are unable to propagate on host cells at a level normally achieved by wild-type adenovirus (e.g., Ad2, Ad5) or replication-competent adenovirus-based vectors. Thus, in a preferred embodiment, the DNA sequence encoding the transcription unit, at least a portion of the adenovirus E3 region, E4ORF3, and at least one other portion of E4, preferably E4ORF4, E4ORF6/7 and/or E4ORF3/4, are provided together (i.e. in cis) on a single replication-defective adenovirus vector. A number of replication defective adenovirus vectors are known in the field including vectors deficient in E1 region function such as those adenovirus vectors lacking the E1a and E1b regions.

The components of a transgene expression system according to the invention can be configured on a single replication-defective adenovirus vector in a number of ways. For example, as reported in published PCT application WO/9630534 (herein incorporated by reference), it is possible to construct a variety of adenovirus vectors in which a transcription unit comprising a transgene (i.e., expression cassette) is positioned in the E1a and E1b region of the adenovirus vector and an E4 region cassette is positioned in the E4 region. However, in other adenovirus vectors, the expression cassette is positioned in the E4 region and the E4 cassette is positioned in the E1a, E1b regions.

Thus, in accordance with the invention, the transcription unit comprising the transgene is constructed and inserted into an adenovirus vector in accordance with conventional recombinant DNA methods. A particularly preferred insertion site is the E1a, E1b region of the adenovirus vector. In that same vector, the adenovirus E3 region portion and the E4 cassette are preferably positioned in the E3 and E4 regions of the adenovirus vector, respectively.

Alternatively, the transcription unit comprising the transgene may be inserted in the E4 region of the adenovirus vector and the E4 cassette can advantageously be inserted in the E1a, E1b region of the adenovirus vector. In such a case, the E3 cassette is preferably positioned, e.g., in the E3 region of the adenovirus vector.

In a preferred embodiment of the invention, the transcription unit comprising the transgene is inserted in an E1a, E1b region of an adenovirus vector. In this embodiment, the transcription unit and the adenovirus E3 region portion are provided on a single adenovirus vector, separated by adenovirus genome sequence comprising the E2 region. The adenovirus vector is further provided with at least a portion of the adenovirus E3 region, E4ORF3, and at least one other portion of E4, preferably E4ORF4, E4ORF6/7 and/or E4ORF3/4, positioned distally to the adenovirus E3 region of the vector relative to the direction of adenovirus major late transcription portions. The adenovirus vector is capable of providing persistent transgene expression and protecting transduced cells from damaging or destructive cell-mediated immune response by expressing the transgene in the presence of expression from at least a portion of the adenovirus E3 region and at least E4ORF3 and E4ORF4 and/or other portions of the adenovirus E4 region.

Expression of the transgene is augmented by an operably linked eukaryotic or viral transcriptional control elements such as promoters, enhancers, and other control elements suitable for use with adenovirus vectors. Preferably, a strong promoter is linked 5' to the transgene so as to drive transgene expression in a variety of cell types. For example, a strong promoter particularly suited for use with the E4ORF3 gene product (e.g., the cytomegalovirus (CMV) promoter) may be included so as to enforce transgene expression. In such embodiments, the transgene also includes DNA encoding one or more RNA processing signals, preferably a polyadenylation segment.

Additionally, in preferred embodiments, the transcription unit further comprises sequence modifications that reduce production of replication-competent adenovirus during laboratory propagation of the adenovirus vector and further provide for making clinical-grade preparations thereof (see e.g., Guo et al. supra).

The E3 cassette in the adenovirus vector may comprise a full length E3 region. Alternatively, the E3 cassette may constitute a portion of the E3 region, preferably a portion capable of adversely effecting operation of major histocompatibility class I (MHC class I) molecules in cells expressing the transgene expression system. For example, the gp19K gene product of the E3 region, has been shown to down-regulate MHC presentation. A reduction or elimination of MHC presentation in cells containing the transgene expression systems of the invention augments the persistence of the transgene by reducing or eliminating susceptibility to cell-mediated immune responses against the cells. Examples of E3 cassettes comprising the gp19K region have been disclosed in a co-pending U.S. Patent Application entitled "Novel Adenovirus Vectors Capable of Facilitating Increased Persistence of Transgene Expression" filed on Apr. 14, 1997, the disclosure of which is incorporated herein by reference. See also co-pending application "Novel Transgene Expression Systems For Increased Persistence" filed concurrently herewith, the disclosure of which is incorporated by reference. In addition, the 14.7, 10.4 and 14.5 k proteins of E3 may also be included to provide additional protection against lysis by TNF-α (see Wold et al., *Virology* 184:1–8 (1991)).

As noted, in addition to the E3 region or portion thereof, the vector contains E4ORF3 and at least one other portion of E4, preferably E4ORF4, E4ORF6/7 and/or E4ORF3/4. Preferred parts of the E4 cassette are E4ORF3 and E4ORF4, E4ORF3 and E4ORF6/7, and E4ORF3/4. The most preferred embodiment includes E3, E4ORF3, and E4ORF4. The next most preferred embodiment includes E3, E4ORF3, and E4ORF6/7.

The transgene expression systems of the present invention can be configured one more than one DNA construct. For example, the DNA sequence encoding the transcription unit, at least a portion of the adenovirus E3 region, the E4ORF3 segment or portion thereof, and the E4ORF4 and/or other portion of the adenovirus E4 region may preferably be provided on the same DNA construct, e.g., a replication deficient adenovirus vector. In such embodiments, a user of the present invention can readily handle and introduce the components of the transgene expression system simultaneously into cells. Thus it is preferred that the DNA sequence encoding the transcription unit, and the required regions of the adenovirus be included together on a single adenovirus vector.

However, it is also an object of the present invention to provide the components of the transgene expression system on separate DNA constructs, e.g., plasmids, adenovirus vectors, recombinant adenovirus derived from the adenovirus vectors and combinations thereof, thereby giving the user control over administration of the transgene expression system. Particularly, this approach is advantageous in several settings, e.g., in instances where it is desirable to introduce components of the transgene expression system to cells at different times.

For example, the DNA sequence encoding the transcription unit may alternatively be included on a single plasmid, and the adenovirus E3 and E4 cassettes may be included on a separate adenovirus vector. In other embodiments, the DNA sequence encoding the transcription unit and the E3 cassette region is included on a plasmid and the E4 cassette is included on a separate adenovirus vector. Alternatively, the DNA sequence encoding the transcription unit and the adenovirus E4 cassette may be included in the plasmid, and the adenovirus E3 region may be included on the adenovirus vector. In addition to plasmids, components of the transgene expression system can be provided on a circular DNA capable of autonomous replication e.g., in a bacterial host such as a phagemid, cosmid, episome, or the like.

Additionally, the components of the transgene expression system can be positioned on one or more suitable plasmids, phagemids, cosmids, or episomes.

In one embodiment of the present invention, a transgene expression system described previously is provided as a complex comprising at least one cationic amphiphile to facilitate delivery and entry into of the transgene expression system to target cells. In a preferred embodiment, the transgene expression system is provided as a pharmaceutical composition comprising the transgene expression system, preferably as a complex comprising the transgene expression system and at least one cationic amphiphile, in which the pharmaceutical composition is capable of alleviating a chronic or hereditary disease including those disorders or diseases afflicting mammalian respiratory tissue (e.g., cystic fibrosis).

In other embodiments of the present invention, the pharmaceutical composition comprises a transgene expression system comprising at least a portion of the E3 region, the E4ORF3 and at least one other portion of E4, preferably E4ORF4, E4ORF6/7 and/or E4ORF3/4, together with a pharmaceutically acceptable carrier. The pharmaceutical composition may comprise a transgene expression system capable of reducing expression of MHC Class I receptor in cells containing that system, thereby improving longevity of transgene expression. The pharmaceutical composition may comprise a transgene expression system in which the E3 region of the transgene expression system comprises at least the DNA sequence encoding gp19K protein. In another embodiment, the pharmaceutical composition comprises a transgene expression system in which the E3 region consists of DNA sequence encoding of gp19K, 14.7 k, 10.4 k and 14.5 k proteins and the E4 cassette consists of E4ORF3 and E4ORF4. Preferably, the transgene is operably linked to a eukaryotic viral promoter, such as the CMV or a PGK promoter, preferably the CMV promoter. The transgene preferably comprises a gene which is capable of expressing a gene product which can alleviate disease or disorder such as occurring in mammalian respiratory tissue. In preferred embodiments, the pharmaceutical composition comprises a transgene expression system in which the transgene is a wild-type copy of the cystic fibrosis transmembrane regulator gene.

In accordance with the present invention, there is provided a method of making a pharmaceutical composition as described previously, in which the method comprises combining the transgene expression system with one or more cationic amphiphiles sufficient to form the pharmaceutical composition.

The invention is also directed to methods for the production of the transgene expression system, as further described below.

The present invention further provides methods for expressing a transgene in a mammal and reducing or eliminating susceptibility to cell-mediated immune responses against cells expressing the transgene in which the method comprises combining a transgene expression system of the invention claim with one or more suitable cationic amphiphiles to form a complex, administering a therapeutically effective amount of the complex to cells in the mammal, contacting the cells with the complex under conditions sufficient to transform the cells and express the transgene in the cells, and reducing or eliminating susceptibility to the cell-mediated immune response by expressing the transgene in the presence of an expressed E3 cassette and a modified E4 cassette in accordance with this invention.

BRIEF DESCRIPTION OF THE DRAWINGS

FIG. 1A shows the structure of the entire adenovirus genome. FIG. 1B shows an expanded view of the genomic structure of the adenovirus E4 region including structure of an E4+ (A), E4ORF3 (B), and E4ORF3, ORF4 (C) regions.

DETAILED DESCRIPTION OF THE INVENTION

Figure 1A:
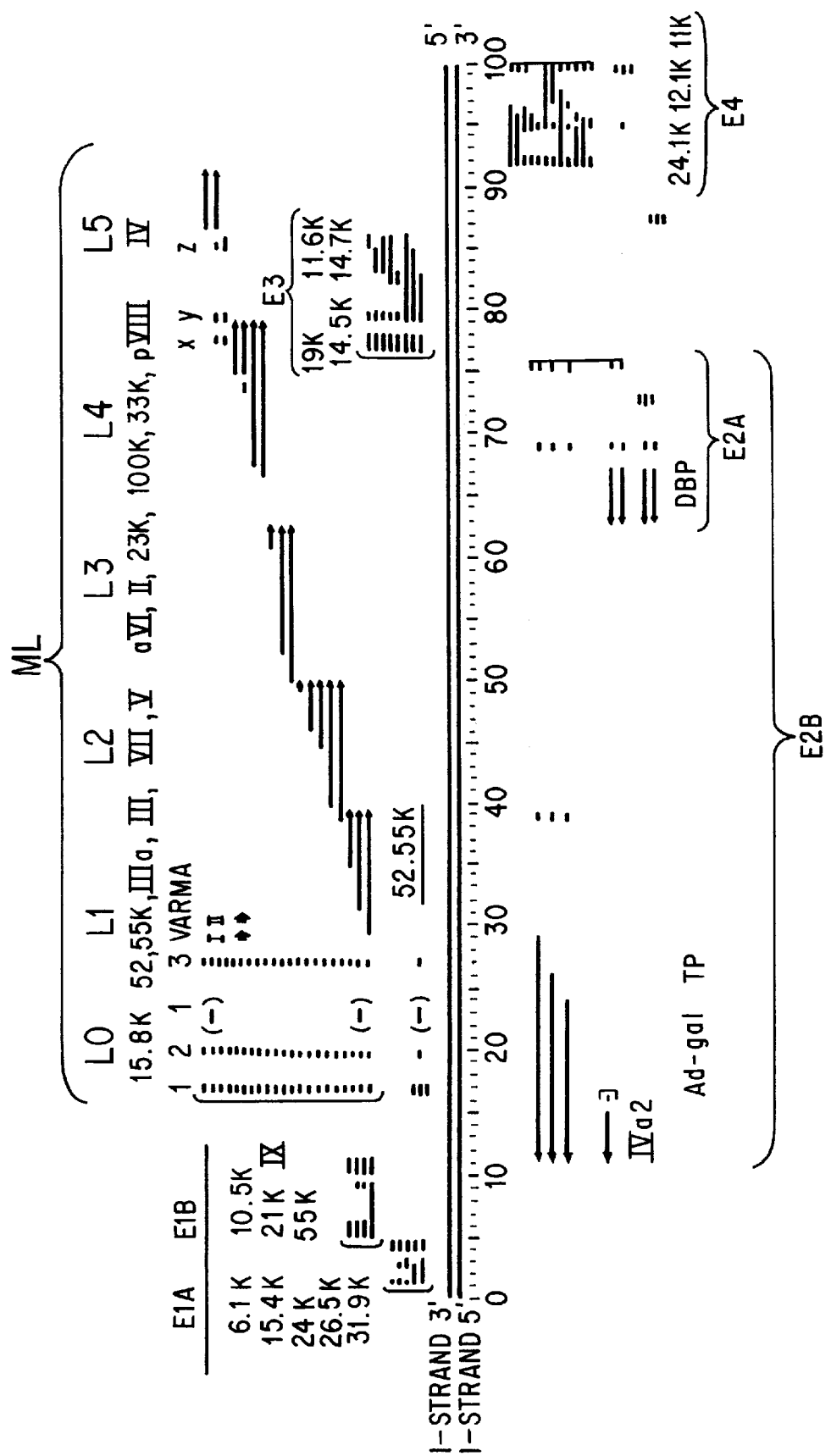
FIGS. 1A and 1B are schematic diagrams of the genomic structure of adenovirus.

The present invention features adenovirus transgene expression systems, related pharmaceutical compositions and methods of making and using them. In one embodiment, the adenovirus transgene expression system features a transgene expression system comprising DNA sequences encoding a transcription unit comprising a transgene operably linked to expression control sequences, at least a portion of the adenovirus E3 region ("E3 cassette"), and E4ORF3 and at least one other portion of E4 ("E4 cassette"). The transgene expression system is capable of persistently expressing the transgene in cells in vitro and in vivo and reducing or eliminating susceptibility to cell-mediated immune reactions against cells expressing the transgene.

Preferably the components of the adenovirus transgene expression system (i.e. the transcription unit, E3 cassette, E4 cassette) are configured on a single adenovirus vector. Preferably, the adenovirus vector is replication-defective. This is not intended to be limiting of the transgene expression systems, since the components can be configured in a number of ways to meet the intended use. For example, in one preferred embodiment, the adenovirus vector comprises a transcription unit comprising the transgene inserted into the E1a, E1b region of adenovirus. In this embodiment, the adenovirus vector further comprises the E3 cassette and the E4 cassette configured in positions corresponding to the E3 and E4 regions of adenovirus, respectively.

The adenovirus vector largely comprises adenovirus genome sequences, and further comprising at least a portion of an adenovirus E3 region and an E4ORF3 and at least one other portion of E4. Preferably, the adenovirus vector is incapable of productively replicating in host cells unless co-infected with an adenovirus helper virus or introduced into a suitable cell line supplying one or more adenovirus gene products in trans (e.g., 293 cells).

An adenovirus vector according to the invention can belong to any one of the known six human subgroups, e.g., A, B, C, D, E, or F, wherein a preferred series of serotypes (all from subgroup D) includes Ad9, Ad15, Ad17, Ad19, Ad20, Ad22, Ad26, Ad27, Ad28, Ad30, or Ad 39. Preferred serotypes include the Ad2 and Ad5 serotypes. Additionally, chimeric adenovirus vectors comprising combinations of Ad DNA from different serotypes are within the scope of the present invention. For example, it is possible to construct a chimeric Ad2 vector with fiber encoding DNA from Ad17 and DNA encoding Ad2 backbone.

Humoral immune responses are believed to play a role in reducing the effectiveness of adenovirus vectors in some settings, e.g., during treatment protocols requiring repeated administration of the vector. Accordingly, it is desirable in some cases to insert a desired transgene into a "panel" of Ad vectors of different serotype (or combinations of serotypes). By serially administering the panel of Ad vectors, each Ad vector serotype comprising the same transgene, it is possible to minimize or preferably eliminate adverse humoral immune reactions. A preferred panel of Ad vectors include those derived from Ad2, Ad5, Ad17, and Ad39 serotypes or chimeric combinations thereof. The panel can be expanded to include additional serotypes as needed and depending, e.g., on the number of dosages required and severity of the immune response encountered.

By the term "transgene" as used herein is meant a DNA segment encoding a protein which is partly or entirely heterologous (i.e. foreign) to the adenovirus genome. The transgene can be a therapeutic transgene that supplies (whole or in part) a necessary gene product that is totally or partially absent from a mammalian cell or tissue of interest. Transgenes encoded by the transcription unit of the adenovirus vector include, but are not limited to, those transgenes encoding enzymes, blood derivatives, hormones, lymphokines such as the interleukins and interferons, coagulants, growth factors, neurotransmitters, tumor suppressors, apolipoproteins, antigens, and antibodies. More particularly, the transgenes may encode CFTR, dystrophin, glucocerebrosidase, tumor necrosis factor, p53, retinoblastoma (Rb), or adenosine deaminase (Ad) genes. Transgenes encoding antisense molecules or ribozymes are also within the scope of the invention.

Particularly, amino acid sequence changes and/or non-sequence modifications to the known CTFR cDNA sequence (see e.g., published PCT Application No. WO 96/30534, the disclosure of which is incorporated by reference), which modifications do not substantially affect the capacity of the CFTR cDNA to function as a chloride channel are within the scope of the present invention. That is, the amino acid sequence changes and/or non-sequence changes (e.g., amino acid deletion, addition, substitution, or addition of carbohydrate, respectively) do not affect the capacity of the CFTR cDNA to exhibit a chloride channel current in vitro.

Preferably, the adenovirus vector comprises components of the transgene expression system necessary to facilitate efficient entry into cells or tissues; to achieve persistent expression of the transgene, and to reduce the destructive impact of cell-mediated immune responses against cells or tissues comprising the transgene expression system. Preferably, the adenovirus vector includes the transgene in a transcription unit which is a DNA sequence encoding the transgene under control of one or more suitable expression control sequences such as a strong viral promoter (e.g., CMV), enhancer, polyadenylation element, and other eukaryotic control elements capable of increasing transgene expression, all of which are operably linked to provide optimal expression of the transgene. In preferred embodiments, the transcription unit includes a strong viral promoter such as a CMV promoter covalently linked 5' to the transgene as part of the transcription unit. By the term "CMV promoter" is meant a promoter existing naturally in a CMV strain having a DNA sequence controlling transcription of the immediate early (IE) gene of CMV. Alternatively, other strong eukaryotic promoters are suitable for such use, including a hybrid promoter such as a CMV/E1a hybrid promoter. Additionally, the adenovirus vector may include other suitable genetic modifications, e.g., to further reduce replication or recombination potential of the adenovirus vector, e.g., displacing the protein IX gene to another location in the viral genome.

In preferred embodiments of the present invention, the transgene also includes DNA encoding one or more eukaryotic RNA processing signals, preferably those RNA processing signals acceptable for use in humans. For example, SV40 small t intron sequences, or the SV40 polyadenylation signal can be used as RNA processing signals. The preferred polyadenylation is SV40 polyadenylation signal. The signals may be positioned proximally and/or distally to DNA coding for the transgene, as desired. The transcription unit may further comprise sequence modifications that reduce production of replication-competent adenovirus and further provide for making clinical-grade preparations thereof. For example, deleted adenovirus protein IX sequences may be positioned between the fiber region and the SV40 and/or BGH polyadenylation signal of the vector encoding the transgene, which decreases the likelihood of recombination events in the complementing cell line (e.g., 293 cells) that can give rise to replication competent virus.

Figure 2A:
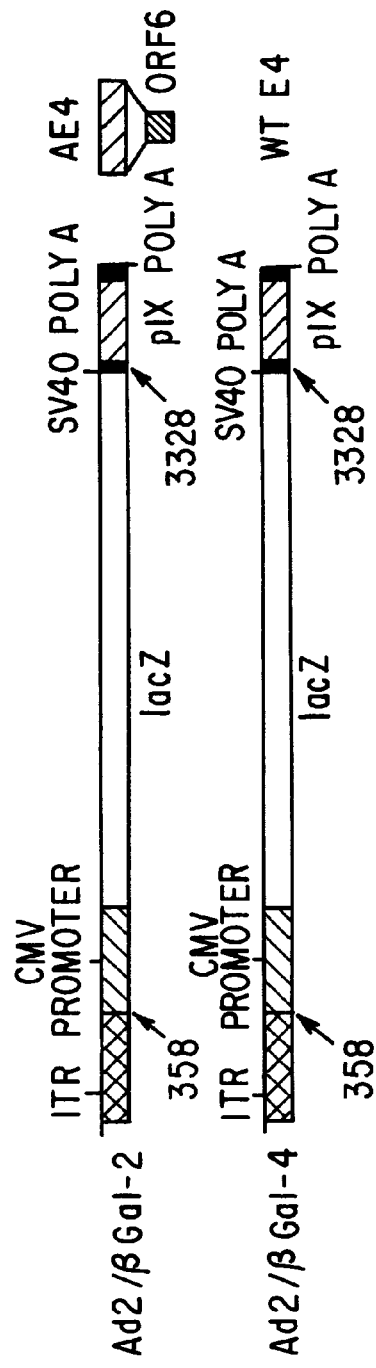
FIGS. 2A and 2B are schematic diagrams showing the structure of adenovirus vectors (Ad2 serotype) comprising the β-galactosidase gene and E4 region or various E4 region deletions. A schematic representation of the adenovirus genome is shown above the vectors shown in each figure. The numbers under "β-gal" in FIG. 2B refer to specific Ad2/β-gal constructs. For example, constructs 2, 4–8, and 11 are E3+ and constructs 9, 10, 12 and 13 are E3−.
Figure 2B:
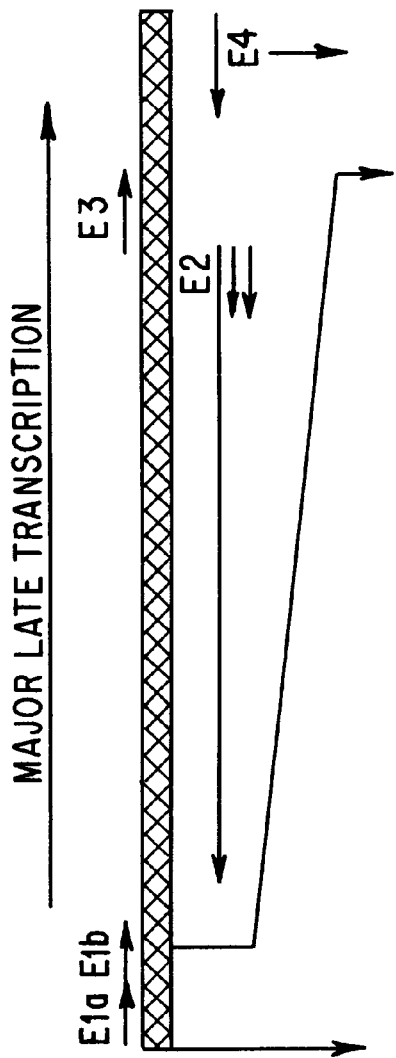
Figure 3:
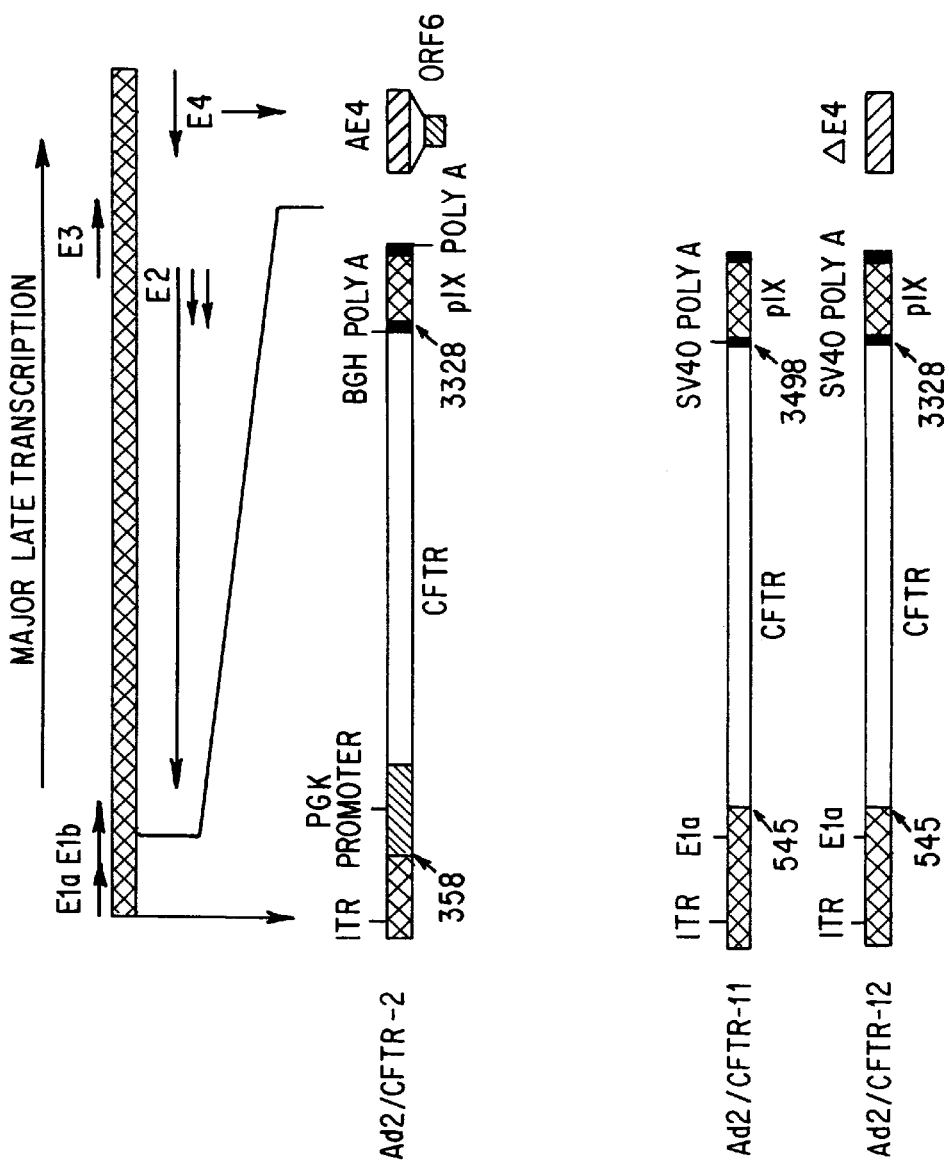
FIG. 3 is a schematic diagram showing the structure of adenovirus vectors (Ad2 serotype) comprising the human CFTR gene and the E4 region or various E4 region deletions. A schematic representation of the adenovirus genome is shown above the adenovirus vectors.

Accordingly, in representative embodiments, the transcription unit of the transgene comprises operably linked in sequence: the CMV promoter/a transgene/SV40 polyadenylation signal/pIX sequence/BGH polyadenylation signal. Exemplary transcription units provided in adenovirus vectors are illustrated in FIGS. 2A, 2B and 3, however, see also Ad2/CFTR-5 as described in WO/96/30504 and structures related to, e.g., Ad2-βgal-7, Ad2-βgal-4 as described in Kaplan, J M et al. (1997) supra as well as other related structures apprarent to those skilled in the art.

For example, an Ad2 vector within the scope of the present invention is one in which a transgene has been inserted into the Ad2-βgal-7 vector after removing the β-galactosidase gene to form Ad2 vectors with an E4ORF4 E4 region.

A further component of the transgene expression system is the E4 cassette. The E4 cassette may include other E4ORFs if desired to further increase persistence of transgene (e.g., E4ORF1, E4ORF2 or E4ORF6). The E4 cassette is preferably provided on a single vector although individual ORFs of the E4 cassettes may be provided on separate vectors as needed. The E4 cassette may be placed under the control of native E4 promoters or alternatively may be placed under the control of heterologous promoters such as CMV. Preferably, the E4 cassette is placed under the control of promoters that causes sufficient expression of the E4 cassette to facilitate persistent expression of the transgene. For example, in one embodiment, the CMV promoter is used to control expression of one or more ORFs in the E4 cassette.

In a particularly preferred embodiment, the transgene expression system is provided with E4ORF3, E4ORF4 in combination with at least an MHC Class I down-regulating portion of E3.

In preferred embodiments, transgene expression is controlled by a strong promoter, preferably the CMV promoter, which promoter is activated by presence of the E4ORF3 region and directs transcription of the transgene encoded by the transcription unit in a non-tissue specific manner. For example, when the transgene is the CFTR, the CMV promoter directs transcription of the transgene in cells or tissues longer in the presence of the E4ORF3 then in the absence thereof. The full-length CMV promoter can be used or a fragment thereof capable of driving transgene expression and being up-regulated by expression from E4ORF3 region. CMV promoter fragments can be tested for capacity to augment persistent expression of the transgene using assays described below. In other embodiments the PGK or other selected promoter is used for direct transcription of the transgene.

A further component of the transgene expression system of the invention is the E3 cassette. The E3 cassette contains several encoded gene products including the gp19K gene product, which is believed to down-regulate MHC Class I expression. It is provided, for example, concurrently with the transcription unit, to a cell in order to facilitate increased persistence. In this invention, persistence of transgene expression is improved at least in part by down-regulating MHC Class I expression afforded by the E3 cassette. The individual open reading frames of the E3 cassette may be placed under the control of native E3 promoters, or alternatively may be placed under the control of heterologous promoters such as those disclosed herein. In one embodiment of the invention, the E3 open reading frame encoding the gp19K protein is placed under control of a promoter that causes sufficient expression of the E3 cassette so that enough protein is available to down-regulate MHC Class I expression. For example, the CMV promoter may be used separately. Another example of a strong promoter suitable for use in accordance with the present invention is the Raus sarcoma virus promoter (RSV).

A "gene product" encoded by the transcription unit, particularly by the transgene, refers to a molecule which is produced as a result of transcription of the transcription unit. Gene products include RNA molecules transcribed from the gene, as well as proteins encoded by the RNA transcribed from the transgene. RNA and protein gene products may or may not be post-synthetically modified. A "wild-type" gene product or protein is encoded by a gene product whose biological activity is indistinguishable from the naturally-occurring gene product found in normal individuals.

The components of the transgene expression system (i.e., transcription unit; E3 cassette; E4 cassette) are delivered to a cell on one or more plasmids, adenovirus vectors, or combinations thereof. For example, in a preferred embodiment, the transcription unit is provided in a recombinant adenovirus comprising an adenovirus vector in which the CMV promoter is positioned 5' (upstream) to the transgene to provide efficient transcription therefrom. The adenovirus E3 cassette of the transgene expression system is provided in cis to the transcription unit on the adenovirus vector. The E4 cassette is preferably provided in cis to the transcription unit and the E3 cassette. This embodiment is advantageous in that a single recombinant adenovirus can deliver the transgene expression system to cells.

The components of the transgene expression system can also be delivered to a cell using a hybrid plasmid/adenovirus delivery system in which some of the components are delivered by plasmid, and other components are delivered on an adenovirus comprising an adenovirus vector. Alternatively, all components can be delivered in plasmids. Delivery can be at different times although in most cases the components will be delivered simultaneously to provide optimal transgene expression in the cells and to reduce the impact of cellular immune responses against cells comprising the transgene expression system. For example, such a hybrid delivery system may contain the transcription unit on the plasmid, and other components of the transgene expression system in an adenovirus vector. In such an embodiment, an amphiphile or other cationic molecule-based delivery system can be utilized to deliver both the plasmid and the recombinant adenovirus virus to desired cells. In another embodiment, the cationic molecule-based delivery can be utilized to deliver the plasmid to a cell after allowing the recombinant adenovirus to infect the cell first. In a preferred embodiment of the invention, both plasmid and recombinant adenovirus virus are co-delivered by the same transfer route, e.g., cationic molecule-based delivery to control stoichiometry of the transgene expression system components.

The adenovirus vectors of the invention can be made in accordance with standard recombinant DNA techniques. In general, the vectors are made by making a plasmid comprising a desired transcription unit inserted into a suitable adenovirus genome fragment. The plasmid is then co-transfected with a linearized viral genome derived from an adenovirus vector of interest and introduced into a recipient cell under conditions favoring homologous recombination between the genomic fragment and the adenovirus vector. Preferably, the transcription unit is engineered into the site of an adenovirus E1 deletion. Accordingly, the transcription unit is inserted into the adenoviral genome at a pre-determined site, creating a recombinant adenoviral vector. The recombinant adenovirus vector is further recombined with additional vectors comprising desired E3 and/or E4 cassettes to produce the adenovirus vectors. The recombinant adenovirus vectors are encapsidated into adenovirus particles as evidenced by the formation of plaques in standard viral plaque assays. Preparation of replication-defective adenovirus stocks can be accomplished using cell lines that complement viral genes deleted from the vector, (e.g., 293 or A549 cells containing the deleted adenovirus E1 genomic sequences). After amplification of plaques in suitable complementing cell lines, the viruses can be recovered by freeze-thawing and subsequently purified using cesium chloride centrifugation. Alternatively, virus purification can be performed using chromatographic techniques. Examples of such techniques can be found for example in published PCT application WO/9630534; and Armentano D., et al., *Human Gene Therapy* 6:1343 (1995) (each reference incorporated herein by reference).

Titers of replication-defective adenoviral vector stocks can be determined by plaque formation in a complementing cell line, e.g., 293 cells. For example, end-point dilution using an antibody to the adenoviral hexon protein may be used to quantitate virus production (Armentano et al., *Human Gene Ther.*, 6:1343–1353 (1995)).

Suitable plasmids for delivering the transcription unit to the linearized viral genome include such vectors as pCMVβ (Clontech, Palo Alto, Calif.), in which a transgene can be placed under the control of the CMV promoter. A variety of adenovirus vectors for delivering E3 and/or E4 cassettes have been disclosed. (See, e.g., Huang, M—M and P. Hearing *J. Virol.*, 63:2605 (1989)). Alternatively, or in addition, the plasmids can be used for delivering other components of the transgene expression system.

Plasmids containing components of the transgene expression system can be constructed using standard recombinant DNA techniques. Large scale production and purification can be performed using techniques well known to those skilled in the art (see, e.g., *Current Protocols in Molecular Biology,* Ausubel et al., eds., John Wiley & Sons, Inc., New York, 1995; Sambrook et al. *Molecular Cloning: A Laboratory Manual* 2ed Cold Spring Harbor Laboratory Press (1989)).

The components of the transgene expression system are preferably contained on plasmids, adenovirus vectors, recombinant adenoviruses and combinations thereof for delivery to a cell. However, the delivery of such components to a cell in the form of naked DNA is also within the scope of the invention, using such routes are electroporation, biolistic transfer, microinjection, delivery mediated by calcium salts, cationic lipids or polybrene, as well as other known DNA transfer methods.

Marker or reporter genes may be used combined with the transgene to detect persistence thereof in transduced cells. Exemplary plasmids comprising markers include plasmids such as pCF1-CAT, comprising the chloramphenicol acetyltransferase (CAT) gene under the control of the CMV promoter, and other plasmids encoding, e.g., β-galactosidase.

In a particularly preferred embodiment, a recombinant adenovirus comprising an adenovirus vector is delivered using mediated delivery, such as with the use of cationic amphiphiles. More specifically, cationic amphiphiles feature a structure that encompasses both polar and non-polar domains so that the molecule is capable of simultaneously facilitating entry across a lipid membrane with a non-polar domain while a cationic polar domain attaches to a biologically useful molecule (typically nucleic acid or protein) to be transported across the membrane of a target cell.

Cationic amphiphiles in accordance with this embodiment are used to form complexes with adenovirus vectors and include, but are not limited to DOTMA (Felgner et al., *Proc. Natl Acad. Sci. USA,* 84:7413–7417 (1987)) (N-[1-(2,3-dioletloxy)propyl]-N,N,N-trimethylammonium chloride); DOGS (dioctadecylamidoglycylspermine) (Behr et al., *Proc. Natl Acad. Sci. USA,* 86:6982–5986 (1989)); DMRIE (1,2-dimyristyloxypropyl-3-dimethylhydroxyethyl ammonium bromide) (Felgner et al., *J. Biol. Chem.,* 269:2550–2561 (1994)); and DC-chol (3B [N-N',N'-dimethylaminoethane)-carbamoyl]cholesterol) (U.S. Pat. No. 5,283,185 to Epand et al.).

Further preferred cationic amphiphiles used to complex with and facilitate transfer of the adenovirus vectors of the invention (as well as other plasmids or viruses described herein) have been disclosed in PCT Publication No. WO 96/18372, published Jun. 20, 1996 (the disclosure of which is hereby incorporated herein by reference), such as GL-67, GL-53, and GL-120. More preferably, the cationic amphiphile used to deliver the adenovirus vector comprises spermine cholesteryl carbamate (GL-67) or GL-120.

The pharmaceutical compositions of the invention which are formulated with one or more cationic amphiphiles may optionally include neutral co-lipids such as dileoylphosphatidylethanolamine(DOPE) to facilitate delivery of the transgene expression system into a cell. In a preferred embodiment of the invention, the cationic amphiphile GL-67 and the neutral co-lipid DOPE are combined in a ratio of about 1:2, respectively, before complexing with a plasmid and/or virus for delivery to a cell. In many instances it is desirable to employ 100% GL-67 and additional compositions described, e.g., in the aforementioned PCT Appl. No. WO/9618372.

In embodiments of the invention where the transcription unit comprising the transgene is contained on one plasmid and the adenovirus E3 cassette and the E4 cassette are included on a single recombinant adenovirus, both plasmid and virus may be complexed, e.g., simultaneously, with a cationic amphiphile for delivery to a cell. For example, the plasmid may be combined with GL-67:DOPE (1:2 ratio), and the adenovirus may be combined with 100% GL-67, and equal volumes may be combined to form the plasmid/virus complex containing all components of the transgene expression system.

Particularly, GL-67:DOPE and plasmid can be combined in about a 0.6 mM to 3.6 mM ratio, respectively. Further, Gl-67 can be combined with recombinant adenovirus in about $5 \times 10 \times 10^5$ molecules per Ad particle.

In general, transgene persistence can be evaluated in vivo or in vitro using several test formats. For example, cell lines can be transfected with plasmids, adenovirus vectors, or infected with recombinant adenoviruses of the invention. These assays generally measure the level and duration of expression of a contained transgene. Examples of such assays have been reported in D. Armentano et al., *J. Virol.* 71:2408 (1997).

Additionally, persistence of transgene expression may also be measured using suitable animal models. Animal models are particularly relevant to assess transgene persistence against a background of potential host immune responses. Such a model may be chosen with reference to such parameters as ease of delivery, identity of transgene, relevant molecular assays, and assessment of clinical status.

Where the transgene encodes a therapeutic protein, an animal model which is representative of a disease state may optimally be used in order to assess clinical improvement.

Relevant animals in which the transgene expression system may be assayed include mice, rats and monkeys. Suitable mouse stains in which the transgene expression system may be tested include C57B1/6 and Balb/c (wild-type and nude) (available from Taconic Farms, Germantown, N.Y.).

Where it is desirable to relate a host immune response to vector administration, testing in immune-competent and immune-deficient animals may be compared. In this instance, adverse responses to the vector administration can be evaluated, especially those mounted by the host immune system. The use of immune-deficient animals, e.g., nude mice, can be used to characterize vector performance and transgene expression independent of an acquired host response, and to identify other determinants of transgene persistence.

The transgene may encode a biologically useful protein and/or may encode a marker protein used to test the transgene expression system. Assays suitable for use to determine persistence of transgene expression include measurement of transgene mRNA (e.g., by Northern blot, S1 analysis, reverse transcription-polymerase chain reaction (RT-PCR)), or incorporation of detectably-labelled nucleotide precursors (e.g., radioactively or fluorescently labelled nucleotide precursors) or by biological assays, such as a plaque assay, e.g., for a transgene encoding an essential viral gene product in a non-permissive cell line). Additionally, presence of a polypeptide or protein encoded by the transgene may be detected by Western blot, immunoprecipitation, immunocytochemistry, radioimmunoassay(RIA)or other techniques known to those skilled in the art.

In one example of the test system, the adenovirus vector includes a CFTR transgene and is administered to the respiratory epithelium of test animals, to evaluate persistence of CFTR expression in the respiratory tract, particularly the lungs of those test animals. Particular test animals of interest include C57B1/6 or Balb/c mice, cotton rats, or Rhesus monkeys. Molecular markers which may be used to determine the persistence of expression include the measurement of CFTR mRNA, by, for example, Northern blot, S1 analysis or RT-PCR as well as other previously mentioned markers. Alternatively, the presence of the CFTR protein in the test animals may be detected by Western blot, immunoprecipitation, immunocytochemistry, or other techniques known to those skilled in the art.

The cationic amphiphile-plasmid complexes or cationic amphiphile-virus complexes may be formulated into pharmaceutical compositions for administration to an individual in need of the delivery of the transgene.

Typically the pharmaceutical compositions are made as described previously by combining the transgene expressions system with one or more suitable cationic amphiphiles sufficient to form a pharmaceutical composition.

The pharmaceutical compositions can include pharmaceutically acceptable carriers, including any relevant physiological solutions. As used herein, "pharmaceutically acceptable carrier" includes any acceptable solution, dispersion media, coating, antibacterial and antifungal agents, isotonic and absorption delaying agents, and the like. Except insofar as any conventional media, carrier or agent is incompatible with the active ingredient, its use in the therapeutic compositions is contemplated.

Routes of administration for the pharmaceutical compositions containing the transgene expression system include conventional and pharmaceutically acceptable routes intranasal, intravenous, intramuscular, subcutaneous, intradermal, oral and other parenteral routes of administration.

The invention is further directed to methods for using the pharmaceutical compositions of the invention in vivo or ex vivo applications in which it is desirable to deliver one or more transgenes into cells for therapeutic purposes. In vivo applications involve the direct administration of the transgene expression system formulated into a pharmaceutical composition to the cells of an individual. Ex vivo applications involve the transfer of the transgene expression system directly to autologous cells which are maintained in vitro, followed by re-administration of the transduced cells to a recipient.

Dosage of the transgene expression system to be administered to an individual for therapeutic benefit is determined with reference to various parameters, including the condition to be treated, the age, weight and clinical status of the individual, and the particular molecular defect requiring therapeutic correction. The dosage is preferably chosen so that administration causes a therapeutically effective result, as measured by molecular assays or clinical markers. For example, determination of the level of expression of the transgene product of interest, as well as persistence of such expression over timea transgene expression system containing the CFTR transgene which is administered to an individual can be performed by molecular assays including the measurement of the CFTR protein produced as detected by Western blot, immunoprecipitation, immunocytochemistry, or other techniques known to those skilled in the art. Relevant clinical studies which can be used to assess therapeutic benefit from delivery of the CFTR transgene include PFT assessment of lung function and radiological evaluation of the lung. Demonstration of the delivery of a transgene encoding CFTR can also be demonstrated by detecting the presence of a functional chloride channel in cells of an individual with cystic fibrosis to whom the vector containing the transgene has been administered (Zabner et al., *J. Clin. Invest.*, 97:1504–1511 (1996)). The persistence of transgene expression in other disease states can be assayed analogously, using the specific clinical parameters most relevant to the condition.

Exemplary dosage ranges for administering viral vectors has been reported (see e.g., Zabner et al. (1996), supra). Accordingly, dosage of an adenovirus vector according to the invention which contains all the components of the transgene expression system will generally fall about within the reported ranges.

It is specially advantageous to formulate parenteral compositions in dosage unit form for ease of administration and uniformity of dosage. Dosage unit form as used herein refers to physically discrete units suited as unitary dosages for the subjects to be treated, each unit containing a predetermined quantity of active ingredient calculated to produce the desired therapeutic effect in association with the required pharmaceutical carrier. The specification for the novel dosage unit forms of the invention are dictated by and directly depend on the unique characteristics of the transgene expression system and the limitations inherent in the art of compounding. The principal active ingredient (the transgene expression system) is compounded for convenient and effective administration in effective amounts with the pharmaceutically acceptable carrier in dosage unit form as discussed above.

Maximum therapeutic benefit from administration of the transgene expression system of the invention may require repeated administration, e.g., as the transformed cells die or lose their ability to express the factors of interest.

The invention also comprises a method of expressing a transgene in a mammal, and protecting cells expressing the transgene from the cell-mediated immune response in which the method comprises combining the transgene expression systems with one or more cationic amphiphiles to form a complex administering a therapeutically effective amount of the complex cells.

The practice of the invention employs, unless otherwise indicated, conventional techniques of protein chemistry, virology, microbiology, recombinant DNA technology, and pharmacology, which are within the skill of the art. Such techniques are explained fully in the literature. See, e.g., *Current Protocols in Molecular Biology*, Ausubel et al., eds. John Wiley & Sons, Inc. New York (1995), and *Remington's Pharmaceutical Sciences*, 17th eds. Mack Publishing Co., Easton, PA, (1985).

The invention is further illustrated by the following specific examples which are not intended in any way to limit the scope of the invention.

The adenovirus genome is illustrated in FIG. 1 and is published in full sequence, e.g., in Roberts, R. J. et al. (1986) in W. Doerfler Ed. *Development in Mol. Virology* 8: (Adenovirus DNA) pp. 1–51 for Ad2, the disclosure of which is hereby incorporated herein by reference.

The following examples outline the preparation and use of Ad2 vectors according to the invention comprising a desired transgene inserted into the adenovirus E1 region. The Ad2 vectors further comprise deletions in the E3 region and/or deletions in the E4 region. Techniques for using the E1 region as a transgene insertion site are known (see e.g., Rich D. P et al. *Hum. Gene Ther* (1993); 4: 461 and references provided therein). All viruses, except those with complete E4 deletions, were propagated in 293 cells, purified and titered by end-point dilution using FITC conjugated anti-hexon antibody (Chemicon) as previously described (Armentano et al., *Hum. Gene Ther.*, 6:1575–1586 (1995)). Both 293 and VK2–20 cells were obtained from Dr. Frank Graham at McMaster Uniersity, Hamilton, Ontario Canada. The 293 cell line is available from American Type Culture Collection, Rockville, Md. (ATCC CRL 1573). Ad2 E4− vectors were propagated in the VK2–20 cell line.

Additional packaging cell lines useful in the practice of the invention, including propagation of E4− vectors have been deposited with the ATCC (Accension nos. CRL 12182 and CRL 12183)

In general, the Ad2 vectors can be made by a variety of methods. For example, standard recombinant DNA techniques and homologous recombination can be used to make the Ad2 vectors described herein. For example, Ad2 vectors comprising one or more E4ORFs from the E4 region can be made by recombinant DNA methods in which a desired E4ORF (or more than one E4ORF) is PCR-amplified using DNA oligonucleotide primers that flank desired E4ORF(s). The PCR-amplified DNA product is then modified with suitable restriction enzyme sites and then ligated into restriction enzyme cleaved Ad2 vector lacking the E4 region. Example 1, below, provides an illustration of this approach for the construction of E1−, E3+ Ad2 vectors comprising a transgene and various E4 modifications. See also Armentano et al. (1995) supra. Related approachs can be used to make E1−Ad2 vectors with E3 modifications. See also Innes et al. (PCR Protocols, Academic Press, Inc., Harcourt Stockton Press) for a discussion of relevent PCR protocols.

Additional Ad2 vectors comprising modified E4ORFs have been reported. For example, Huang, M—M and Hearing, P. supra have disclosed methods of making Ad2 vectors comprising specific E4ORF deletions and insertions. Particularly, the reference discloses methods of making Ad2 vectors with an E4ORF3, E4ORF4, or E4ORF6, insertion into an E4− region. For example, Example 1, below, discloses use of related techniques to incorporate E4ORF deletions into Ad2 vectors.

Examples 3 and 4 below show that E4ORF4 and E4ORF6/7 provide protection against adenovirus specific CTLs in vitro when present in conjunction with the E3 region. To determine whether other ORFs have a related activity, Ad2 vectors comprising those ORFs can be readily made and tested in the adenovirus specific CTL assay to assess anti-cytolytic activity.

Ad2 vectors which were capable of protecting cells against adenovirus CTLs in vitro are subsequently tested in vivo to assess the persistence of transgene expression in the absence or presence of a host immune response. For example, Ad2 vectors described herein can be administered to respiratory epithelia of test rodents or primates (e.g., wild-type or nude mice; cotton rats; monkeys) according to standard procedures (see e.g., Kaplan, J M et al. Gene Therapy (1996) 3, 117, supra; Armentano, D. et al. (1995); supra; Kaplan, J M et al. (1997), supra). Infected test animals can then be followed for peristence of transgene expression by a number of approaches including determing levels of transgene expression in lungs of infected animals by reverse PCR and/or following expression of a reporter gene such as β-galactosidase. It is believed that substantial enhancement of transgene expression is achieved using the vectors of the present invention. Performance levels according to the practice of the invention may be evaluated by protein expression for at least about 2 to 3 weeks, and preferably up to about three to four months. Examples of suitable assays are as follows. For example, the rodent lung assay described below in Example 5 is one way to evaluate performance.

REFERENCE EXAMPLE 1

Construction of the following vectors, plasmids, cassettes, or other components of the present invention follow the disclosure of Armentano, D. et al. (1995), supra; Kaplan, J M. et al. (1997), supra; Kaplan, J. M. et al. (1996); Armentano, D. et al. (1997), supra; and published PCT Application No. WO 96/30535; the disclosures of which are each incorporated herein by reference.

Adenovirus vectors comprising various Ad2/β-gal constructs are illustrated in FIGS. 2A and 2B. In general, the vectors were made as follows.

The CMVβ-gal expression cassette was constructed in a pBR322-based plasmid that contained Ad2 nucleotides 1–10,680 from which nucleotides 357–3328 were deleted. The deleted sequences were replaced with a cytomegalovirus immediate early promoter (obtained from pRC/CMV, Invitrogen,), a lacZ gene encoding β-galactosidase with a nuclear localization signal, and an SV40 polyadenylation signal (nucleotides 2533–2729). The lacZ gene was obtained as a NotI fragment from pCMVβ (Clontech, Palo Alto, Calif.). The CMV promoter fragment in the Ad2/β-gal vector series contains CMV promoter sequences from −523 to −14. This is smaller than the fragment that is in pCMVβ from Invitrogen (619 bp Thai fragment).

The Ad2/β-gal-2 vector was made generally according to previously described methods (see Armentano, D. et al. supra). Briefly, the CMVβ-gal expression cassette was restriction digested and ligated to linearized and dephosphorylated Ad2E4ORF6. The ligated vector was then transfected into 293 cells to generate virus stocks.

Construction of the Ad2E4ORF6 vector has been described (see Armentano, D. et al. (1995) supra).

Briefly, Ad2 sequences between nucleotides 32,815 and 35,577 were deleted, removing all open reading frames of E4 but leaving the E4 promoter, E4 cap sites, and the first 32–37 nucleotides of E4 mRNA intact as well as the polyadenylation signal and cleavage site for fiber mRNA. A DNA fragment (nucleotides 33,178–34,082) encompassing the E4ORF6 coding region (nucleotides 33,195–34,077) was derived by PCR and was used to replace the deleted sequences. Additional sequences in the PCR primers included restriction sites at the 5' and 3' ends of the ORF6 fragment (ClaI and Bam HI respectively) and a synthetic polyadenylation sequence for mRNA processing. The construction of Ad2ORF6 was accomplished as follows by using standard cloning protocols (see e.g., Ausubel et al. supra and Sambrook et al. 1989). The ORF6 PCR fragment and a DNA fragment containing the inverted terminal repeat (ITR) and the E4 promoter region (nucleotides 35,597–35,937) were cloned into pBluescriptIIsk+ (Stragene) to create pORF6. A fragment from pORF6 containing the ITR and ORF 6 was ligated to sequences in plasmid pADΔE4 which contains Ad2 nucleotides 28,562–32,815 to generate pADORF6. pADORF6 was digested with PacI (Ad2 nucleotide 28,612) and ligated to Ad2 DNA digested with PacI and AseI. 293 cells were transfected with the ligation mixture and the resulting virus, which has only been modified in the E4 region, was analyzed with appropriate restriction enzymes to confirm the genomic structure.

Construction of a complete E4 deletion (ΔE4) has been described (see Armentano D. et al. (1997), supra).

Briefly, the pAdORF6 vector was cut with BamHI and SalI which removes the ITR and E4ORF6. This segment was replaced with a BAMHI-BglI fragment containing the SV40 polyadenylation signal and a BamHI-SalI fragment generated by PCR containing Ad nucleotides 35642 to 35937 (E4 enhancer region and ITR).

The Ad2/β-gal-5 vector comprises a deleted E4 region as described in published PCT application No. 96/30534. The Ad2/,β-gal-4 vector is identical to Ad2/,β-gal-2 except for the E4 region which is not deleted (E4+).

EXAMPLE 1

Construction of Ad2/β-Gal constructs

Additional Ad2/β-gal constructs as illustrated in FIG. 2B were made as follows.

Ad2/β-gal-7 was made in VK2–20 cells by recombination of the large PacI fragment of Ad2/β-gal-2 (corresponding to the left end of the virus) with the large PmeI fragment of d1366+ORF4 (corresponding to the right end). Ad2/β-gal-8 through −13 were similarly made in 293 cells using Ad2/β-gal-5 for recombination. Ad2/β-gal-8 was made by recombination with E4d1ORF1-4 which contains only ORFs 6 and 6/7. Viruses with knock outs of individual ORFs, Ad2/β-gal-9 (ORF1), Ad2/β-gal-10 (ORF2), Ad2/β-gal-11 (ORF3), Ad2/β-gal-12 (ORF4) and Ad2/β-gal-13 (ORF6/7) were derived from in 351, in 352, E4 in E4ORF3, d1358, and d1356 respectively.

Ad2/β-gal-4 E3Δ2.9 comprises an intact E4 region. Construction of the Ad2/β-gal2E3Δ1.9 vector was prepared by methods described in the co-pending U.S. Application (filed on Apr. 14, 1997; the disclosure of which is incorporated by reference).

Briefly, the adenovirus E3 region comprises ORFs encoding the 12.5K, 6.7K, gp19K, 11.6K, 10.4K, 14.5K and 14.7K gene products (see e.g., Tollefson et al. *J. Virol.* (1996) 70: 2296; Tollefson et al. *Virology* (1996) 220: 152 and references cited therein). Ad2 vectors comprising a at least the gp19K ORF can be made according to several techniques. For example, by using conventional recombinant DNA techniques (e.g., restriction digestion and ligation), the pAd/E4+E3Δ1.6 plasmid was made in a Bluescript backbone. This plasmid comprises the 12.5K, 6.7K and gp19K ORFs and lacks the 11.6K, 10.4K, 14.5K and 14.7K ORFs of E3. Plasmid pAd/E4+E3A1.6 contains the right hand end of Ad2 from the SpeI site at nucleotide 27123 until the right ITR. Thus, the E3 region in this plasmid comprises a 1549 basepair deletion from nucleotides 29292 to 30840 of E3. Related methods can be used to make other E3 deletions comprising at least the gp19K region.

An Ad2/CMV-CFTR/E3Δ1.6 vector was made by homologous recombination between the plasmid and Ad2/CFTR-5. The construction of Ad2/CFTR-5 has been described in published PCT Appl. WO 96/30534 (the disclosure of which has already been incorporated herein by reference).

REFERENCE EXAMPLE 2

The Ad2/CFTR2 vector is a recombinant adenovirus type 2 (Ad2) vector from which most of the E1 region (nucleotides 357–3,328) has been replaced with a CFTR expression cassette containing a PGK promoter, CFTR cDNA and BGH polyadenylation signal (see FIG. 3). The cDNA for CFTR represents nucleotides 123–4622 of the published sequence. Construction of Ad2/CFTR2 is described in the published International Patent Application corresponding to PCT US 93/11667, the disclosure of which is incorporated by reference. The E3 region is conserved while the E4 region is modified by removal of all open reading frames (between nucleotides 32,815 and 35,577) and replacement with the EF open reading frame 6 (ORF6; nucleotides 33,178–34,082) only (see, for example, Armentano et al., 1995).

An Ad2/CFTR-5 vector has been described in published PCT Application No. WO 96/30534 the disclosure of is incorporated herein by reference. Briefly, the Ad2/CFTR-5 vector comprises a human CFTR cDNA as the transgene under the control of the CMV promoter and the BGH polyA signal, which is inserted at the site of a deletion in the E1 region. The E2 and E3 regions of Ad2/CFTR-5 contain wild-type adenovirus serotype 2 sequences and all E4 sequences have been deleted except for E4ORF6. The Ad2/CFTR-5 vector can be used to make a variety of Ad2 vectors by homologous recombination in, e.g., 293 cells. For example, as described in Example 2 an Ad2/CMV-CFTR/E3Δ1.6 vector comprises E2 and E4 regions and a 1549 basepair deletion in E3 can be generated by homologous recombination between pAd/E4+/E3Δ1.6 and Ad2/CFTR-5.

EXAMPLE 2

Construction of Ad2/CFTR Constructs

Additional Ad2/CFTR constructs were made as follows.

Figure 1B:
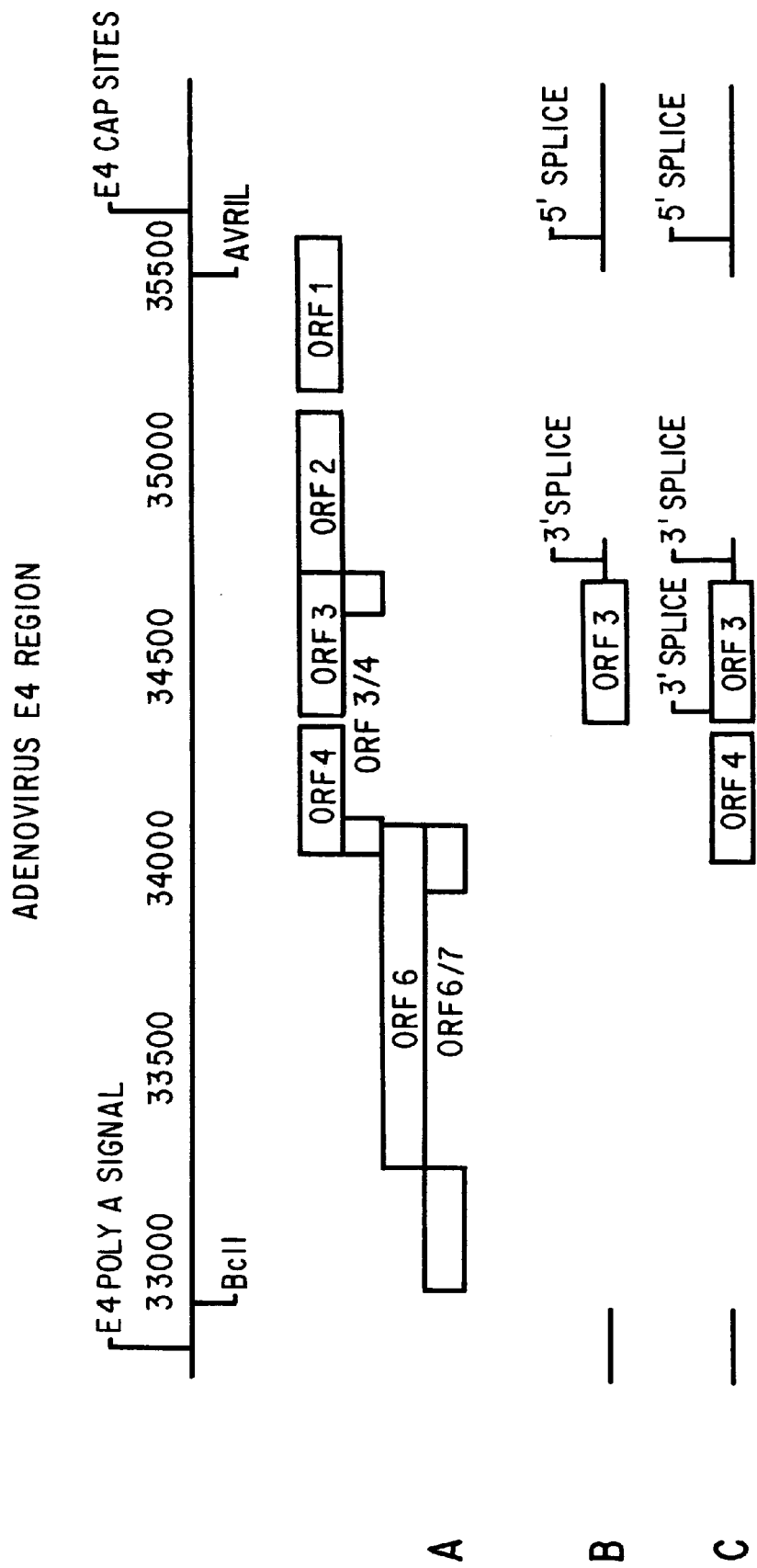

FIG. 1B (A) depicts the organization of the open reading frames in the E4 region of adenovirus type 2. (B) and (C) of FIG. 1B depict the structure of viruses that contain E4ORF3 or E4ORF3 and E4ORF4 respectively. Plasmids containing E4ORF3 and E4ORF3 and E4ORF4 expression cassettes were derived from pAbE4 which contains Ad2 sequences from 27123 to 35937 cloned into the SpeI and HindIII sites of pBluesccriptIIsk+ (Stratagene). To construct an E4ORF3 containing plasmid, sequences between the AvrII site (nucleotide 35470) and the BclI site (nucleotide 32891) in pAbE4 were deleted and replaced with a PCR generated AvrII-BamHI fragment (nucleotides 34804 to 34356). This fragment contained the coding sequence for E4ORF3 and a 3' splice site.

An E4ORF3 and E4ORF4 containing plasmid was similarly constructed by replacing deleted E4 sequences with PCR generated AvrII-BamHI fragment (nucleotides 34804 to 33998). This fragment contained the coding sequences for E4ORF3 and E4ORF4 as well as 3' splice sites for E4ORF3 and E4ORF4 expression. The resulting plasmids, pAbE4ORF3 and pAbE4ORF3+4 can then be linearized with EagI for recombination with, e.g. PacI cut AbCFTR-5 to make a virus that is modified in E4 to contain only E4ORF3 or E4ORF3 and E4ORF4, respectively. Published PCT Application No. WO 96/30534 describes the construction of the Ad2CFTR-5 and is incorporated herein by reference.

EXAMPLE 3

E3$^+$ Ad2/β-galactoside constructs Protect Against Lysis in the Presence of E4, E4ORF4 or E4ORF6/ 7.

The Ad2 β-gal constructs shown in FIGS. 2A and 2B were tested for capacity to provide protection against lysis in a cytotoxic T cell assay reported by Kaplan, J M et al. (1997), supra.

Briefly, to evaluate cytotoxic T lymphocyte (CTL) activity, spleen cells from animals treated with Ad (3–4 mice/group) were pooled and stimulated in vitro with mitomycin C-inactivated, infected syngeneic fibroblasts. Cells were cultured in 24-well plates containing $5 \times 10^6$ spleen cells and $6 \times 10^4$ stimulator fibroblasts per well in a 2-ml volume. The culture medium consisted of RPMI-1640 medium (GIBCO BRL, Grand Island, N.Y.) supplemented with 100 U/ml penicillin, 100 μg/ml streptomycin, 2 mM glutamine, $5 \times 10^{-5}$ M 2-mercaptoethanol, 20 mM HEPES buffer, and 10% heat-inactivated fetal calf serum (Hyclone Laboratories, Ic., Logan, Utah). Cytolytic activity was assayed after 5–7 days of culture. Target fibroblasts were infected with vector at a multiplicity of infection (m.o.i.) of 100 for 48 hours and were treated with 100 U/ml recombinant mouse interferon-γ (Genzyme, Cambridge, Mass.) for the last 24 hours to enhance MHC Class I expression and antigen presentation to effector CTLs. The fibroblasts were labeled with Chromium-51 ($^{51}$Cr; New England Nuclear, Boston, Mass.) overnight (50 μCi/$10^5$ cells) and added to the wells of a round-bottomed 96-well plate in a 100-μl volume ($5 \times 10^3$ fibroblasts/well). Effector cells were added in a 100-μl volume at various effector/target cell ratios in triplicate. After 5 hours of incubation at 37° C./5% $CO_2$, 100 μl of cell-free supernatant was collected from each well and counted in a Packard Multi-Prias gamma counter (Downers Grove, Ill.)./ The amount of $^{51}$Cr spontaneously released was obtained by incubating target fibroblasts in medium alone and the total amount of $^{51}$Cr incorporated was determined by adding 1% Triton X-100 in distilled water. The percentage lysis was calculated as follows: % Lysis– [(Sample cpm)–(Spontaneous cpm)]/[(Total cpm)–(Spontaneous cpm)]×100. As a control for nonspecific lysis (e.g., by natural killer cells or tumor necrosis factor-α), naive spleen cells stimulated with infected fibroblasts, or vector-primed spleen cells incubated alone were tested in parallel and routinely gave rise a negligible percent lysis values of 10% or less. The assay to assay variability for CTL activity measured under the same set of conditions was within 10–20%.

Figure 4:
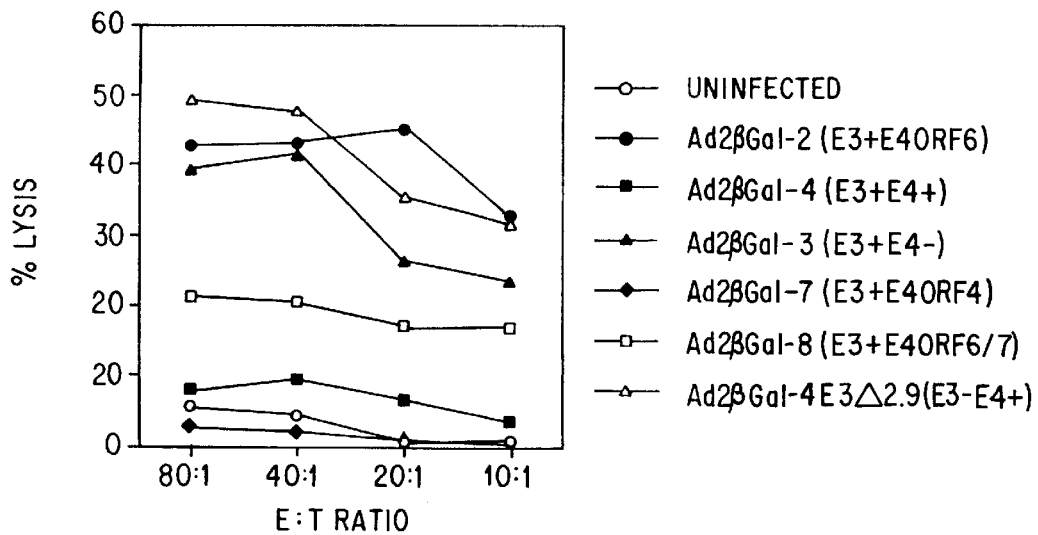
FIG. 4 is a graph showing that cells transduced with adenovirus vectors comprising the β-galactoside gene, the adenovirus E3 region, and the adenovirus E4 region or E4ORF4 are protected from lysis by adenovirus-specific cytotoxic T-lymphocytes (CTLs). Adenovirus vectors comprising the E3 region and E4ORF6/7 provided intermediate protection.

The results shown in FIG. 4 are consistent with E3 providing protection against lysis in the presence of E4ORF4. E3 also provided protection against lysis when combined with wild type E4. From these results the E3+EFORF6/7 combination also appeared to provide protection. These results were confirmed in subsequent experiments and in some of these the E4ORF6/7 gave better protection than shown in FIG. 4. However, as previously discussed, the use of E3+E4+ vectors containinng the entire E4 region resulted in difficulty in vector replication, owing to the length of the genome.

EXAMPLE 4

E3$^+$ Ad2/CFTR constructs Protect Against Lysis in the Presence of E4.

Figure 5:
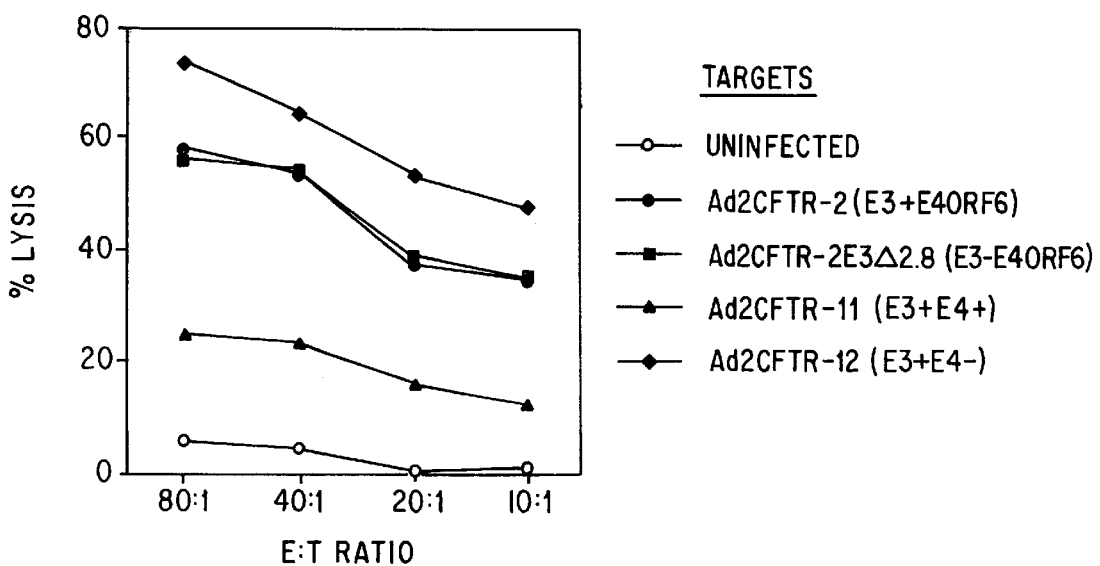
FIG. 5 is a graph showing that cells transduced with adenovirus vectors comprising the CFTR gene, the adenovirus E3 region, and the adenovirus E4 region are protected from lysis by adenovirus specific CTLs.
Figure 6:
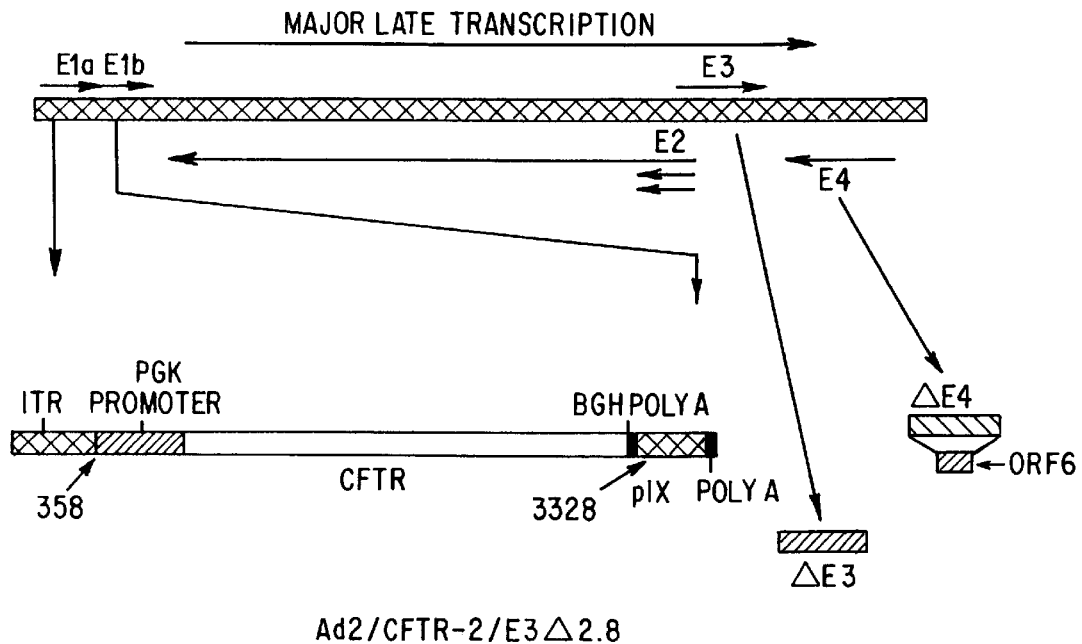
FIG. 6 is a drawing showing the structure of the Ad2/CFTR-2/E3Δ2–8 vector.
Figure 7:
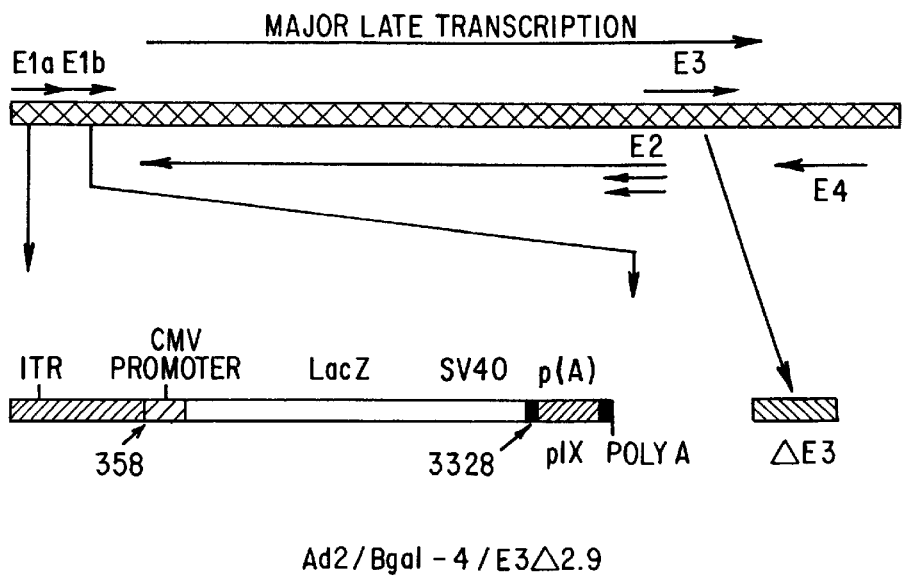
FIG. 7 is a drawing showing the structure of the Ad2/β-Gal-4/E3Δ2–9 vector.

The E3+Ad2/CFTR vectors shown in FIG. 3 were tested in CTL experiments described in Example 3 above. FIG. 5 shows that the data are consistent with E3 providing protection against lysis in the present of wild type E4.

EXAMPLE 5

Persistence of β-galactosidase expression in mouse lung and rat hepatocytes.

The following is an example of an assay that can be used to assess persistence of transgene expression.

For example, to assess persistence of transgene expression in the absence of a host immune response, a series of adenovirus vector constructs expressing β-galactosidase were used to infect rat hapatocytes in vitro or were administered intranasally to nude BALB/c mice.

Balb/c parental and nude mice were purchased from Taconic Farms (Germantown, N.Y.). Animals, mostly females, ranging from 7 to 16 weeks old were used for in vivo studies.

Rat hepatocytes were infected with vectors from the β-gal series (see FIGS. 2A and 2B) at an MOI of about 10. β-galactosidase expression was visualized by X-gal staining on days 3 and 14 post-infection. β-galactosidase vectors including a wild-type E4 deletion or knocked out for E4ORF1,2,4, or 6/7 showed persistent expression of β-galactosidase. In contrast, expression was lost in cells infected with an E4ORF3 knockout. These findings indicate that ORF3 from the E4 region enhances persistent of transgene expression under control of the CMV promoter.

This in vitro finding is supported by in vivo studies in which nude BALB c/mice were instilled intranasally with $3 \times 10^9$ i./u. of a vector series including Ad2/βGal4 (wild-type E4), Ad2/βGal7 (E4ORF4), Ad2/βGal-8 (E4ORF6,6/7), Ad2/βGal-9 (E4ORF1 knockout), Ad2/βGal10 (E4ORF2 knockout), Ad2/,βGal-11 (E4ORF3 knockout) and Ad2/βGal-13 (E4ORF6/7 knockout). Mice were anesthetized by inhalation of Metofane (methoxyflurane) and were instilled intranasally with of $3 \times 10^9$ i.u. (infectious units) of recombinant virus in 100μl PBS, 3% sucrose. Mice were sacrificed on days 3 and 14 post-instillation and βGalactosidase activity was measured in the lung using the Galactolight assay (Tropix). Persistent expression was observed out to 14 days in mice that received vector containing wild-type E4 or vectors in which E4ORFs 1,2 or 6/7 were disrupted. Transgene expression was lost in mice receiving an adenovirus vector containing only E4ORF4 or E4ORF6,6/7 or in mice instilled with an E4ORF3 knock-out vector. Therefore, as was observed with rat hepatocytes in vitro, these finding are consistent with a requirement for E4ORF4 in order to achieve persistence of expression in vivo.

The data indicate that, in the absence of a host immune response, E4ORF3 is required to achieve persistence of βGalactosidase expression. The E4ORF3 region is, however, unlikely to be sufficient to achieve long term expression in an immunocompetent host since cell mediated immune responses directed against transduced cells have been reported to terminate transgene expression in many systems. The inclusion of E4ORF4 or E4ORF6/7, in addition to E4ORF3, in combination with E3 or a portion thereof (e.g., including gp19K) would be expected to provide protection against lysis by adenovirus-specific CTLs as previously described (see e.g., Examples 3 and 4) and improve persistence of transgene expression.

Lungs from individual animals were homogenized and β-galactosidase activity was measured by an AMPGD assay (Galactolight, Tropix, Waltham, MA). The protein concentration in lung homogenates was measured with the BioRad DC reagent and β-galactosidase activity is expressed as relative light units (RLU/µg protein).

The wild type E4 region is required to achieve longevity of expression from the CMV promoter in mouse lung and in cultured primary rat hepatocytes. Subsequent experiments were aimed at identifying which ORF(s) of E4 are required for this effect. One approach is to construct and test vectors in which the E4 coding region has been replaced with individual E4 ORFs. Another approach is to construct and test vectors in which individual E4ORFs have been disrupted by either insertional or deletion mutagenesis.

The invention has been described with reference to preferred embodiments thereof. However, it will be appreciated that those skilled in the art, upon consideration of this disclosure, may make modification and improvements within the spirit and scope of the invention.

What is claimed is:

1. A transgene expression construct comprising a combination of (a) a DNA comprising a transcription unit which comprises a transgene operably linked to expression control sequences, (b) at least a portion of an adenovirus E3 region, and (c) a modified E4 region containing F4ORF3, and at least one other portion of an adenovirus E4 region, said DNA, E3 region, and modified E4 region being located on a same nucleic acid molecule (in cis) or on a different nucleic acid (in trans).

2. The transgene expression construct of claim 1, wherein the DNA sequence encoding the transcription unit, the adenovirus E3 region, and the E4ORF3 and at least one other portion of E4 are included on an adenovirus vector.

3. The transgene expression construct of claim 1, wherein the DNA comprising the transcription unit is included on a plasmid, and the adenovirus E3 region and the E4ORF3 and at least one other portion of E4 are included on an adenovirus vector.

4. The transgene expression construct of claim 1, wherein the DNA comprising the transcription unit and the adenovirus E3 region are included on a plasmid and the E4ORF3 and at least one other portion of E4 are included on an adenovirus vector.

5. The transgene expression construct of claim 1, wherein the DNA comprising the transcription unit and the E4ORF3 and at least one other portion of E4 are included on a plasmid and the adenovirus E3 region is included on an adenovirus vector.

6. The transgene expression construct of claim 1, wherein the modified E4 region includes E4ORF3 and at least one other portion selected from the group consisting of E4ORF4, E4ORF6/7 and E4ORF3/4.

7. The transgene expression construct of claim 1, wherein the modified E4 region comprises E4ORF3 and E4ORF4.

8. The transgene expression construct of claim 1, wherein the modified E4 region comprises E4ORF3 and E4ORF6/7.

9. The transgene expression construct of claim 1, wherein the E3 region may reduce expression of major histocompatibility class I receptor in cells comprising the transgene expression construct.

10. The transgene expression construct of claim 1, wherein the expression control sequence comprises a cytomegalovirus or polyglycerol kinase promoter.

11. The transgene expression construct of claim 1, wherein the transgene is a wild-type copy of the cystic fibrosis transmembrane regulator gene.

12. A complex comprising the transgene expression construct of claim 1 and at least one cationic amphiphile.

13. The transgene expression system of claim 8, wherein the E3 region of the transgene expression construct comprises DNA encoding gp19K protein.

14. The transgene expression construct of claim 8, wherein the E3 region comprises DNA encoding gp19K protein and the E4ORF3 further comprises E4ORF4.

15. The complex of claim 12, wherein the cationic amphiphile is [GL-67] spermine cholesteryl carbamate.

* * * * *